United States Patent
Gilbert et al.

(10) Patent No.: US 7,217,536 B2
(45) Date of Patent: May 15, 2007

(54) MEDIUM AND METHOD FOR DETECTING/IDENTIFYING MICROORGANISMS

(75) Inventors: Sandra Gilbert, Lyons (FR); Céline Roger-Dalbert, Vaux-en-Bugey (FR); Sylvain Orenga, Neuville sur Ain (FR)

(73) Assignee: Bio Merieux, Marcy l'Etoile (FR)

( * ) Notice: Subject to any disclaimer, the term of this patent is extended or adjusted under 35 U.S.C. 154(b) by 385 days.

(21) Appl. No.: 10/416,591

(22) PCT Filed: Nov. 16, 2001

(86) PCT No.: PCT/FR01/03611

§ 371 (c)(1), (2), (4) Date: Jun. 24, 2003

(87) PCT Pub. No.: WO02/40706

PCT Pub. Date: May 23, 2002

(65) Prior Publication Data

US 2005/0014215 A1    Jan. 20, 2005

(30) Foreign Application Priority Data

Nov. 17, 2000  (FR)  .................................. 00 14879

(51) Int. Cl.
  *C12Q 1/04* (2006.01)
(52) U.S. Cl. .......................................... 435/34; 435/29
(58) Field of Classification Search ................ 435/34, 435/29
  See application file for complete search history.

(56) References Cited

U.S. PATENT DOCUMENTS

| | | | | |
|---|---|---|---|---|
| 3,878,050 A * | 4/1975 | Lee | ................................ | 435/14 |
| 4,717,658 A | 1/1988 | Michaels | ...................... | 435/19 |
| 4,906,573 A * | 3/1990 | Barney et al. | ............... | 435/243 |
| 4,927,927 A | 5/1990 | Goswami et al. | ............... | 97/18 |
| 4,994,376 A | 2/1991 | Zambon et al. | ................ | 435/24 |
| 5,296,370 A | 3/1994 | Martin et al. | ............. | 435/252.1 |
| 5,534,415 A | 7/1996 | Orenga | .......................... | 435/34 |
| 5,786,167 A | 7/1998 | Tuompo et al. | ................ | 435/34 |
| 5,871,944 A * | 2/1999 | Miller et al. | ................ | 435/7.35 |
| 5,962,251 A | 10/1999 | Rambauch | .................... | 435/34 |
| 6,340,573 B1 * | 1/2002 | Armstrong et al. | ............ | 435/18 |
| 2004/0048326 A1 * | 3/2004 | Roger-Dalbert | ............... | 435/19 |

FOREIGN PATENT DOCUMENTS

| | | |
|---|---|---|
| EP | 544 605 A1 | 6/1993 |
| FR | 2 697 028 | 4/1994 |
| WO | WO 94/09152 | 4/1994 |
| WO | WO 95/04157 | 2/1995 |
| WO | WO 99/41409 * | 8/1999 |

OTHER PUBLICATIONS

Cooke, V. et al. A Novel Chromogenic Ester Agar Medium for Detection of Salmonellae. Applied Environmental Microbiology, 65(2)807-812, Feb. 1999.*

Manafi, "New Developments in Chromogenic and Fluorogenic Culture Media", *Int'l J of Food Microbiology*, 60 pp. 205-218 (2000).

Cooke et al., "A Novel Chromogenic Ester Agar Medium for Detection of Salmonellae", *Appl. Environ. Microbio.* vol. 62, No. 2, pp. 807-812 (Feb. 1999).

International Search Report dated Jul. 5, 2002, PCT/FR01/03611.

* cited by examiner

*Primary Examiner*—Ralph Gitomer
(74) *Attorney, Agent, or Firm*—McCracken & Frank LLP

(57) ABSTRACT

A medium for biological analysis by biochemical means involving chromogenic or fluorogenic substrates that react with enzymes (esterases and/or osidases and/or peptidases and/or sulfatases and/or phosphatases) specific for the target strains is that is in a stable, ready-to-use liquid or gel form and contains at least one emulsifying stabilizer of the fatty acid sorbitan ester/fatty acid type and at least one solvent (dimethyl sulfoxide). This medium is obtained by mixing a stock solution of esterase and/or osidase and/or peptidase and/or sulfatase and/or phosphatase substrates in the solvent, and the emulsifying stabilizer, with some of the constituents of the culture medium.

16 Claims, No Drawings

MEDIUM AND METHOD FOR DETECTING/IDENTIFYING MICROORGANISMS

This application is a National Stage application filed under Rule 371 from PCT/FR01/03611 filed Nov. 16, 2001 which claims priority from France 00/14879 filed Nov. 17, 2000.

The field of the invention is that of microbiological analysis by biochemical means and in particular the detection and identification of bacterial strains by the inoculation of reaction media, particularly nutrient media. The latter comprise chromogenic or fluorogenic substrates that are capable of reacting with enzymes specific for the target strains to produce a coloration or a fluorescence for each colony in question.

Of more particular interest within the framework of the present invention is the detection/identification of pathogenic or quality-indicating microorganisms, whether in a medical or industrial environment, and more particularly microorganisms with an enzymatic activity of the esterase, osidase, peptidase, sulfatase or phosphatase type, for example bacteria or yeasts of the genera *Salmonella, Pseudomonas, Listeria, Staphylococcus, Enterococcus* and *Candida* and more particularly those of the species *Escherichia coli, Listeria monocytogenes, Staphylococcus aureus* and *Candida albicans*.

The presence of strains of *Escherichia coli* is often demonstrated by revealing an enzymatic activity of the osidase type, such as β-glucuronidase or β-galactosidase activity.

Likewise, the genus *Listeria* is detected by revealing the presence of β-glucosidase activity.

An aminopeptidase activity can also be utilized to reveal a group, a genus or a species of microorganisms. Alanine aminopeptidase activity, for example, makes it possible to differentiate between Gram-negative bacteria and Gram-positive bacteria.

The genus *Salmonella*, which is responsible for a variety of infections (typhoid fever, food poisoning) in humans, possesses non-specific esterases capable of hydrolyzing chromogenic, for example indigogenic, synthetic substrates.

The detection/identification of *salmonellae*, and more generally of bacteria with esterase activity, is conventionally carried out on gelose or liquid isolating media that allow the detection/identification of suspect colonies of bacteria with esterase activity, especially *salmonellae*. The inoculation of such media is effected by immersing said medium in the sample analyzed or by bringing the sample into contact with the medium.

In their enzymatic makeup, bacteria with esterase, osidase, peptidase, sulfatase or phosphatase activities possess esterases, osidases, peptidases, sulfatases or phosphatases which cleave the target linkages of the substrates present in the medium and thus release the activated chromophoric or fluorophoric part of said substrates. This results in a coloration or a fluorescence that reveals hydrolysis and hence the presence of target bacteria or colonies of target bacteria.

To be able to perform routine tests on a large scale, it is necessary for the detection/identification media to be stable and to enable the corresponding detection/identification methods to be simplified as far as possible by limiting the manipulations. Also, it is important for the methods to offer a high sensitivity (high intensity of coloration) and a first order specificity. Another fundamental parameter of these types of media and methods for the detection/identification of bacteria exhibiting the above-mentioned enzymatic activities is the rate at which the suspect colonies are revealed.

Now, it is known that substrates of enzyme such as esterases, osidases, peptidases, sulfatases or phosphatases present problems of compatibility with culture media for microorganisms, particularly bacteria, possessing these activities. Furthermore, such substrates are not stable over time, meaning that the sensitivity towards the enzymatic activity in question decreases with storage time.

In this context the scientific article entitled "*Synthèse de substrats indigogéniques. Mise en évidence de l'activité estérasique des salmonelles*" ("*Synthesis of indigogenic substrates. Demonstration of the esterase activity of salmonellae*"): A. Agban et al., *Eur. J. Med. Chem.* (1990) 25, 697–699, discloses gelose culture media comprising indigogenic substrates, namely 5-bromoindoxyl pelargonate (C9) in particular, and a bile salt, namely sodium deoxycholate. Such culture media suffer from the same disadvantages as those referred to below with reference to patent document FR 2 697 028.

Patent FR 2 697 028 discloses a culture medium for revealing the presence of *salmonellae* which comprises a chromogenic esterase substrate consisting of an ester of caprylic acid with an indole radical (5-bromo-4-chloro-3-indolyl caprylate), together with a detergent selected from bile salts (sodium deoxycholate). This chromogen and this bile salt are contained in a nutrient medium that allows *salmonellae* to grow. According to the teaching of FR 2 697 028, the bile salt is added directly to the selective medium already containing the esterase substrate.

Another disadvantage associated with the use of bile salts derives from the fact that they are starting materials of animal origin, which vary in quality.

In addition, the results in terms of biological activity are capable of improvement.

This culture medium does not offer all the desirable guarantees in terms of stability of the esterase substrate. Moreover, the latter proves to be incompletely miscible with the culture medium, which obviously detracts from the quality of the results obtained from the point of view of sensitivity, rapidity and stability.

It must also be noted that the culture medium according to FR 2 697 028 is in the form of a powder. This means that the user first has to carry out an operation to reconstitute the liquid or gelled medium. This constraint is a consequence of the lack of stability of the esterase substrates used. In addition, the gelose medium prepared according to the teaching of FR 2 697 028 is not translucent, which is likely to compromise the reading of the colorations associated with any colonies of target bacteria.

PCT patent application WO-92/17607 relates to a detection medium for *salmonellae* which contains TERGITOL-4® (7-ethyl-2-methyl-4-undecanoate hydrogensulfate or its sodium salt). This additive is supposed to improve the selectivity of the detection medium towards target *salmonellae*. The concentration of TERGITOL-4® can vary from 2 to 30 ml/l in the culture medium based on agar gelose/xylose/lysine. According to said document, the detection of *salmonellae* is based solely on a principle of selective growth by competition.

PCT patent application WO-99/41409 relates to chromogenic esterase substrates for the detection of *salmonellae*.

Said document proposes the use of a chromogenic compound which reacts with an esterase/lipase specific for the genus *Salmonella* and having an affinity for C8 fatty acid esters. The chromogenic compound in question comprises an anion and a cation of the formula [4-[2-(4-octanoyloxy-3,5-dimethoxyphenyl)vinyl]-quinolinium-1-(propan-3-yl-) carboxylate]+,-[bromide or chloride]. More precisely, the substrates used are C8 esters, for example, of the carboxylate cation.

Also, the method according to WO-99/41409 describes the use of a sorbitan fatty acid ester (particularly the monolauric acid ester TWEEN® 20). These products are employed as detergents at a rate of 2 g per liter of medium.

In addition, the specific substrate according to the teaching of said PCT patent application can be introduced into the nutrient culture medium as a mixture with methanol, ethanol or N,N-dimethylformamide (DMF). The detergent, if used, is introduced separately rather than together with the substrate and the solvent.

Whatever the case may be, the means disclosed in WO-99/41409 are not presented as providing an improvement in the stability of the enzyme substrates contained in the detection medium.

Various documents also disclose culture media containing several substrates for the detection of a single enzymatic activity, as well as culture media containing several substrates for the detection of different enzymatic activities.

Patent document WO-95/04157, for example, describes culture media containing different chromogenic osidase substrates such as 5-bromo-4-chloro-3-indoxylgalactoside, 5-bromo-4-chloro-3-indoxylglucuronide, 5-bromo-4-chloro-3-indoxylglucoside or 6-chloro-3-indoxylgalactoside. Such media are used to differentiate especially between bacteria of the species *Escherichia coli* and other coliform bacteria.

Said document further describes a medium containing chromogenic substrates specific for different enzymes such as osidases and phosphatases. Examples of these substrates are 5-bromo-4-chloro-3-indoxyl N-acetyl-glucosaminide and 5-bromo-6-chloro-3-indoxyl phosphate. Such a medium makes it possible in particular to differentiate between *Candida albicans* and other yeasts of the genus *Candida*.

Patent document WO-00/53799 describes a chromogenic medium for the detection of *Staphylococcus aureus* bacteria. This medium contains two chromogenic substrates in combination, especially 5-bromo-4-chloro-3-indo-xyl-glucoside and 5-bromo-6-chloro-3-indoxyl phosphate. The principal purpose of such a medium is avoiding false positives or false negatives and differentiating between *S. aureus* and other species or other genera such as *Streptococcus*.

However, patent documents WO-95/04157 and WO-00/53799 give no indication that the media described were developed in order to improve the stability of the enzyme substrates they contain.

Fatty acid sorbitan esters (FASE) are known surfactants that are widely used especially in food and pharmaceutical preparations. By way of illustration, there may be mentioned the article by DICKINSON et al. in "*J. Colloid Interface Sci.* 1999 Apr. 15; 212 (2): 466–473", which relates to the stabilization of emulsions containing sodium caseinate and a polyethoxylated sorbitan monolaurate containing 20 units of ethylene oxide (TWEEN 20). The emulsions in question are oil-in-water emulsions (30% by volume of n-tetradecane at pH 6.8). This technical field is relatively remote from that of the detection of bacteria with specific enzymatic activity by means of a color reaction on a selective culture medium.

The article by GRAM et al. in "*Clin. Chem.* 1985 Oct.; 31 (10): 1683–8" concerns the use of polyethoxylated sorbitan monooleate (TWEEN 80) in an antithrombin-III assay medium, said medium also containing polyethylene glycol, a solution of thrombin and synthetic chromogenic peptide substrates. The additives used are presented as allowing an increase in the concentration of active thrombin so as to guarantee that the analysis performs well. Once again, one is forced to observe that technical concerns of this kind are very different from those peculiar to a medium for the detection of bacteria with specific enzymatic activity using selective culture media containing chromogenic substrates.

In such a technical environment, one of the essential objectives of the present invention is to provide a medium for the detection/identification of bacteria with an enzymatic activity selected from esterase and/or osidase and/or peptidase and/or sulfatase and/or phosphatase activities which is made up in such a way as to optimize the sensitivity of the analysis, i.e. maximize the intensity of the coloration or fluorescence revealing the presence of target bacteria.

Another essential objective of the present invention is to provide a medium for the detection/identification of microorganisms, especially bacteria or yeasts, with an enzymatic activity selected from esterase and/or osidase and/or peptidase and/or sulfatase and/or phosphatase activities which is perfectly translucent before inoculation with the sample to be analyzed.

Another essential objective of the invention is to provide a medium for the detection/identification of microorganisms, especially bacteria or yeasts, with an enzymatic activity selected from esterase and/or osidase and/or peptidase and/or sulfatase and/or phosphatase activities which contains at least one chromogenic or fluorogenic enzyme substrate selected from esterase substrates and/or osidase substrates and/or peptidase substrates and/or sulfatase substrates and/or phosphatase substrates and is storage stable (intensity of the revealed coloration or fluorescence maintained at a maximum level for at least several weeks).

Another essential objective of the invention is to provide a medium for the detection/identification of microorganisms, especially bacteria or yeasts, with an enzymatic activity selected from esterase and/or osidase and/or peptidase and/or sulfatase and/or phosphatase activities which is not in the form of a dry powder that has to be reconstituted with a liquid in order to reconstitute a liquid or gelled medium, but which exists directly in ready-to-use forms.

Another essential objective of the invention is to provide a medium for the detection/identification of microorganisms, especially bacteria or yeasts, with an enzymatic activity selected from esterase and/or osidase and/or peptidase and/or sulfatase and/or phosphatase activities which is economic, especially due to the fact that it comprises reduced amounts of one or more chromogenic or fluorogenic enzyme substrates, which are characteristically expensive.

Another essential objective of the invention is to provide a method of obtaining the above-mentioned detection/identification medium which is simple to carry out and economic.

Another essential objective of the present invention is to provide a method for the detection/identification of strains with an enzymatic activity selected from esterase, osidase and/or peptidase and/or sulfatase and/or phosphatase activities which is easy to carry out (routine tests), economic (amount of reagent, handling, label, speed, etc.), reliable, sensitive, specific and reproducible.

Another essential objective of the present invention is to propose the use of a novel stabilizing additive in media for the detection/identification of microorganisms, especially bacteria or yeasts, with an enzymatic activity selected from esterase and/or osidase and/or peptidase and/or sulfatase and/or phosphatase activities, said activity being revealed as a result of a hydrolysis reaction which releases a dye or a fluorescent product.

These and other objectives are achieved by the present invention, which relates first and foremost to a medium for the detection/identification of microorganisms, especially bacteria and/or yeasts, with an enzymatic activity selected from esterase and/or osidase and/or peptidase and/or sulfatase and/or phosphatase activities that is of the type comprising especially a reaction medium, particularly a culture medium, and at least one chromogenic or fluorogenic esterase and/or osidase and/or peptidase and/or sulfatase and/or phosphatase substrate, with the exclusion of substrates comprising a 4-[2-(4-octanoyloxy-3,5-dimethoxyphenyl)-vinyl]quinolinium-1-(propan-3-ylcarboxylic acid) cation and an anion, this detection/identification being based essentially on revealing the presence of the esterase and/or osidase and/or peptidase and/or sulfatase and/or phosphatase activities, . . . said medium:

is in a stable, ready-to-use liquid or gel form; and
contains:

at least one fatty acid sorbitan ester (FASE) or at least one fatty acid (FA) or an FASE/FA mixture (comprising at least one fatty acid sorbitan ester and at least one fatty acid) as an emulsifying stabilizer, and
optionally at least one solvent (S).

A medium for the detection/identification of microorganisms, especially bacteria and/or yeasts, with an enzymatic activity selected from esterase and/or osidase and/or peptidase and/or sulfatase and/or phosphatase activities, according to the invention, can be obtained from the media presented in patent documents WO-95/04157 and WO-00/53799 described above.

The medium according to the invention has the advantage that it is ready to use and is in a liquid or semiliquid (gel) form without presenting a problem in terms of stability. In fact, the esterase and/or osidase and/or peptidase and/or sulfatase and/or phosphatase substrates present in this medium, even though they are known for their tendency to degrade relatively rapidly, are stabilized through the presence of the FASE, FA or FASE/FA emulsifying stabilizer additive.

This additive, optionally associated with the solvent S, brings a further advantage, namely allowing an excellent dissolution of the esterase and/or osidase and/or peptidase and/or sulfatase and/or phosphatase substrates, which are traditionally reluctant to dissolve. This makes it possible to obtain detection/identification media that are translucent before inoculation, thereby making it easier to read the coloration or fluorescence results.

This FASE, FA or FASE/FA additive is relatively inexpensive and makes it possible to simplify the procedure and to reduce the amount of substrates used (stabilization), resulting in a definite saving in economic terms.

Finally, the means according to the invention give rise to an improvement in the biological activity of the aforementioned substrates, resulting in a more intense coloration of the target colonies and a better specificity.

It is to the inventors' credit to have selected this particular class of emulsifying stabilizers, particularly FASE, which surprisingly and unexpectedly afford properties of stability, translucence, biological activity, sensitivity, reliability and specificity that are altogether apposite in the microbiological analysis by biochemical means according to the invention.

According to one noteworthy characteristic of the invention, the detection/identification medium to which it relates is obtained by mixing at least one stock solution of the substrate in the solvent S with FASE, FA or an FASE/FA mixture, and with at least some of the constituents of the culture medium.

In fact, it appears to be important according to the invention to solubilize the esterase and/or osidase and/or peptidase and/or sulfatase and/or phosphatase substrate in the solvent S in the presence of one or more FASE or FA or an FASE/FA mixture as defined above. This mixture of FASE, FA or FASE/FA substrate and solvent S is then incorporated into at least part of the culture medium, which is preferably in a supercooled gelled form. It has been found that this operating characteristic makes it possible to optimize the advantageous results produced by the means according to the invention.

Preferably, the FASE is selected from the group comprising:

polyethoxylated sorbitan monolaurate containing 20 units of ethylene oxide (EO)—TWEEN® 20-;
polyethoxylated sorbitan monopalmitate (20 EO)—TWEEN® 40-;
polyethoxylated sorbitan monostearate (20 EO)—TWEEN® 60-;
polyethoxylated sorbitan tristearate (20 EO)—TWEEN® 65-;
polyethoxylated sorbitan monooleate (20 EO)—TWEEN® 80-;
polyethoxylated sorbitan sesquioleate (20 EO)—TWEEN® 83-;
polyethoxylated sorbitan trioleate (20 EO)—TWEEN® 85-; and
mixtures thereof, and the FA is selected from the group comprising C4–C20 saturated or unsaturated fatty acids, preferably C6–C11 saturated or unsaturated fatty acids and particularly preferably C8–C9 fatty acids, and mixtures thereof.

The products particularly selected according to the invention are sorbitan esters that are widely used in the food and cosmetic industries as non-ionic emulsifiers, but hitherto they have never been employed in microbiological detection/identification media as stabilizers for esterase and/or osidase and/or peptidase and/or sulfatase and/or phosphatase substrates.

The Hydrophilic-Lipophilic Balances (HLB) of the above-mentioned FASE are respectively 8.6, 6.7, 4.7, 2.1, 4.3, 3.7 and 1.8.

In one advantageous variant of the invention, the emulsifying stabilizer(s) described above, in particular the FASE(s), can be associated with at least one synergistic co-agent, preferably at least one anionic surfactant and particularly preferably 7-ethyl-2-methyl-4-undecyl hydrogensulfate or its salts, more particularly its sodium salts (TERGITOL-4®).

The use of such a synergistic co-agent makes it easier to reveal the presence of the enzymatic activity in the target bacteria. Said co-agent is an excellent complement to the emulsifying stabilizer(s) and particularly the FASE. It makes it possible to improve the selectivity and the detection of the esterase and/or osidase and/or peptidase and/or sulfatase and/or phosphatase activities in the target microorganisms without detracting from the expression of other enzymatic activities which might possibly be used to reveal the presence of the target microorganisms in question. Without wishing to be bound by theory, it is assumed that the synergistic co-agent TERGITOL-4® has an action which favors the penetration of the chromogenic or fluorogenic esterase and/or osidase and/or peptidase and/or sulfatase and/or phosphatase substrates or the excretion of the enzymes across the membranes of the cells of the target microorganisms, thereby optimizing the accessibility of these substrates in respect of the enzymes whose activity is sought. This makes it possible to reduce the amount of substrates used and derive a definite economic advantage therefrom.

Even more preferably, the combination of TWEEN® and TERGITOL-4® seems to be totally effective in the detection/identification medium according to the invention.

The chromogenic or fluorogenic substrate, consisting of a target part for the enzyme and a chromophoric or fluorophoric part, is advantageously chosen from substrates whose target part is selected from the group comprising the following in particular:

glycosides consisting of mono-, di- and/or polysaccharide units linked in the α- or β-position to the hydroxyl group of the chromophoric or fluorophoric part;

α-amino acids or peptides;

organic acids such as —O—CO(CH$_2$)$_n$—CH$_3$, where n is between 0 and 20; and a sulfate, a phosphate, a pyrosulfate, a pyrophosphate and a phosphodiester, and whose chromophoric or fluorophoric part is selected from the group comprising the following in particular:

quinones/anthraquinones and derivatives, especially dihydroxyanthraquinone (alizarin);

amino- and hydroxycoumarins and derivatives;

fluoresceins and derivatives; and indoxyls and derivatives.

Examples of esterase substrates which may be mentioned are chromogenic ester substrates derived from indole, especially 5-bromo-3-indolyl nonanoate, 6-chloro-3-indolyl nonanoate or 5-bromo-3-indolyl decanoate.

2-Alizarin octanoate may be mentioned as an example of a chromogenic esterase substrate derived from anthraquinone.

Examples of osidase substrates which may be mentioned are chromogenic osidase substrates derived from indole, especially 6-chloro-3-indolyl-β-galactoside, 5-bromo-4-chloro-3-indolyl-β-N-acetylglucosaminide or 5-bromo-6-chloro-α-glucoside.

2-Alizarin-β-glucuronide may be mentioned as an example of a chromogenic osidase substrate derived from anthraquinone.

Fluorogenic osidase substrates which may be mentioned are substrates derived from hydroxycoumarin, especially 4-methylumbelliferone-β-glucoside.

Substrates derived from indole may be mentioned as chromogenic peptidase substrates.

Fluorogenic peptidase substrates are especially substrates derived from hydroxycoumarin, such as alanylaminomethylcoumarin.

Sulfatase substrates which may be mentioned are chromogenic substrates derived from indole, particularly 5-bromo-4-chloro-3-indolyl sulfate. 4-Methylumbelliferone sulfate is an example of a fluorogenic sulfatase substrate.

In an equivalent manner, phosphatase substrates which may be mentioned are chromogenic substrates derived from indole, such as 5-bromo-4-chloro-3-indolyl phosphate. 4-Methylumbelliferone phosphate is an example of a fluorogenic phosphatase substrate.

The solvent S is an auxiliary for solubilizing the enzyme substrate of interest, particularly a chromogenic enzyme substrate. It also complements the action of the FASE, FA or FASE/FA emulsifying stabilizer. It is therefore preferably a constituent of the medium according to the invention.

According to an advantageous provision of the invention, the solvent S is selected from the group comprising:

alcohols, preferably methanol, ethanol and methoxyethanol;

amides, preferably dimethylformamide (DMF);

sulfur-containing solvents, preferably dimethyl sulfoxide (DMSO);

aqueous solvents, preferably water and buffered water; and mixtures thereof.

In practice, the solvents preferably used are methanol, DMF and DMSO.

It has been found altogether advantageous according to the invention for the proportion by weight of fatty acid sorbitan ester(s) (FASE) to solvent (S) to be between 20:80 and 80:20, preferably between 30:70 and 70:30 and particularly preferably 40:60 or 60:40.

Still from the quantitative point of view, it is preferable for the concentration of (FASE) in the medium to be defined as follows (in % by weight):

|   |   |
|---|---|
| preferably | $0.1 \leq$ [FASE] $\leq 10$, |
| and particularly preferably | $0.5 \leq$ [FASE] $\leq 5$, |
|  | $1.5 \leq$ [FASE] $\leq 3.5$. |

The amounts of chromogenic or fluorogenic substrate used are such that its concentration in the medium is defined as follows (in mg/l):

|   |   |
|---|---|
| preferably | $1 \leq$ [substrate] $\leq 2000$, |
| and particularly preferably | $5 \leq$ [substrate] $\leq 1500$, |
|  | $25 \leq$ [substrate] $\leq 1000$. |

The amounts of substrate used in the solution of FASE and solvents S are such that its concentration in the medium is defined as follows (in g/l):

|   |   |
|---|---|
| preferably | $0.5 \leq$ [substrate in stock solution] $\leq 2000$, |
| and particularly preferably | $1 \leq$ [substrate in stock solution] $\leq 1000$, |
|  | $2 \leq$ [substrate in stock solution] $\leq 200$. |

As regards the culture medium present in the detection/identification medium, it can be specified that it is selected from the group comprising:

selective media of the type comprising MacConkey, Columbia ANC, PALCAM and Sabouraud gentamycin-chloramphenicol media, preferably MacConkey medium; and non-selective media of the type comprising Columbia +/− blood, trypcase soya, nutrient gelose and Sabouraud media, preferably Columbia medium.

In practice, those skilled in the art will choose the culture medium according to the target bacteria and according to perfectly known criteria with which they are familiar.

Without implying a limitation, it is found that the medium according to the invention is particularly suitable for the detection/identification of microorganisms of medical or industrial interest, especially those of the genus *Salmonella, Pseudomonas, Listeria, Staphylococcus, Enterococcus* or *Candida*.

In the case of the detection of bacteria of the genus *Salmonella*, MacConkey medium, for example, will be chosen as the culture medium.

Furthermore, the medium according to the invention can optionally contain other additives such as one or more other enzyme substrates, for example chromogenic or fluorogenic enzyme substrates, peptones, one or more growth factors, carbohydrates, one or more selective agents, buffers and one or more gelling agents.

The medium according to the invention is in the form of a liquid or gel that is ready to use, i.e. ready for inoculation in a tube or flask or on Petri dishes.

The medium according to the invention can be stored in its containers for several weeks at 40° C. in liquid or gel form.

According to another of its features, the present invention further relates to a method of obtaining the medium as defined above, characterized in that it consists essentially in:
preparing at least one stock solution of the chromogenic or fluorogenic esterase and/or osidase and/or peptidase and/or sulfatase and/or phosphatase substrate in the solvent S and of at least one FASE, FA or FASE/FA mixture,
adding this solution and any other additives to the culture medium, and
homogenizing the whole.

The stock solution is prepared separately by successively incorporating the substrate, the solvent S and the FASE, FA or FASE/FA mixture, optionally containing co-additives. The products and the amounts used are as defined above.

After homogenization, the stock solution is added to the supercooled gelled culture medium which has been regenerated in water beforehand. The medium can also be a non-gelled liquid medium, for example a nutrient broth.

Mixing of the culture medium and the stock solution gives the liquid or gelled detection medium ready for inoculation.

According to yet another of its features, the invention further relates to a method for the detection/identification of strains with esterase and/or osidase and/or peptidase and/or sulfatase and/or phosphatase activity which consists in:
inoculating the detection/identification medium as defined above, either as a product per se or as a product obtained by the method also described above, with the sample containing the target bacteria to be analyzed;
incubating the inoculated medium under appropriate conditions known to those skilled in the art; and
reading/interpreting the colorations or fluorescences of the colonies which have developed after incubation, for example in an oven at 37° C., these colorations revealing hydrolysis of the chromogenic or fluorogenic esterase and/or osidase and/or peptidase and/or sulfatase and/or phosphatase substrate by the target bacteria.

Finally, the invention further relates to the use of fatty acid sorbitan ester(s) (FASE), fatty acids (FA) or an FASE/FA mixture as an emulsifying stabilizer for a medium (liquid or gel) for the detection/identification of microorganisms, especially bacteria or yeasts, with an enzymatic activity selected from esterase and/or osidase and/or peptidase and/or sulfatase and/or phosphatase activities, this medium comprising especially a reaction medium and at least one chromogenic or fluorogenic esterase and/or osidase and/or peptidase and/or sulfatase and/or phosphatase substrate, with the exclusion of substrates comprising a 4-[2-(4-octanoyloxy-3,5-dimethoxyphenyl)vinyl]quinolinium-1-(propan-3-yl)carboxylate and an anion, optionally in association with at least one solvent S for the chromogenic or fluorogenic esterase and/or osidase and/or peptidase and/or sulfatase and/or phosphatase substrate present in the medium.

The Examples which follow will provide a clearer understanding of the invention and make it possible to assess all its advantages as well as its diverse embodiments and modes of implementation.

EXAMPLES

Example 1

Testing the Solubility of the Indoxyl-Based Esterase Substrate 5-bromo-3-indolyl Nonanoate (Chromogenic Esterase Substrate) in a Gelled Medium Different stock solutions of substrate are prepared in methanol in the presence of no. 3 bile salts (bioMérieux). Different volumes of these solutions are then added to a supercooled gelled medium, namely MacConkey medium (regenerated in water at a concentration of 50 g/l).

The protocol and the appearance of the media are collated in Table 1 below.

TABLE 1

| Medium | 1 | 2 | 3 | 4 | 5 |
| --- | --- | --- | --- | --- | --- |
| Substrate concentration of the stock solution | 100 g/l | 50 g/l | 25 g/l | 12.5 g/l | 6.25 g/l |
| Final substrate concentration of the medium | | | 500 mg/l | | |
| Bile salt concentration of the stock solution | | | 5 g/l | | 2.5 g/l |
| Total bile salt concentration of the medium | | | 7.5 g/l | | 4 g/l |
| Methanol concentration of the medium | 0.5% | 1% | 2% | 4% | 8% |
| Observation of the medium poured into dishes | precipitate in the form of coarse grains | precipitate in the form of smaller grains than in medium 1 | slight precipitate: milky medium | milky medium | milky medium |

The most optically homogeneous media are 3, 4 and 5, being the media in which the methanol concentration is greatest. However, these media have a "milky" appearance, so it would seem that the esterase substrate is in the form of an emulsion.

Example 2

Improving the Solubilization of the Esterase Substrate by Adding Tween® 20 (FASE)

Two different stock solutions of substrate are prepared in methanol as the solvent S, one in the presence of no. 3 bile salts and the other in the presence of no. 3 bile salts and Tween® 20 [polyethoxylated sorbitan monolaurate containing 20 units of ethylene oxide (EO)]. A volume corresponding to a final concentration of 500 mg/l of substrate is then added to a supercooled gelled culture medium, namely MacConkey medium. The protocol and the appearance of the media are collated in Table 2 below.

TABLE 2

| Medium | 1 | 2 |
|---|---|---|
| Substrate concentration of the stock solution | 100 g/l | 40 g/l |
| Final substrate concentration of the medium | 500 mg/l | 500 mg/l |
| Bile salt concentration of the stock solution | 5 g/l | 5 g/l |
| Total bile salt concentration of the medium | 6.5 g/l | 6.5 g/l |
| Concentration of Tween® 20 added to the stock solution of substrate | 0% | 60% |
| Concentration of Tween® 20 added to the medium | 0% | 2.5% |
| Observation of the medium poured into dishes | milky medium | translucent medium |

Medium 2 has a better optical homogeneity than medium 1. The esterase substrate is either completely dissolved or in the form of an emulsion whose micellar particles are no longer visible to the eye.

Example 3

Biological Testing of the Two Media Described in the Previous Example

Microorganisms originating from the Applicant's collection were inoculated onto each of the two media described above from a 0.5 McFarland suspension by isolation in three quadrants. The dishes were incubated at 37°C. for 48 hours. The colonies formed were examined visually after 24 and 48 hours of incubation. The coloration of these colonies and the intensity of this coloration were noted. The results are shown in Table 3 below.

TABLE 3

| Strain | | incubation time | medium 1 color | medium 1 intensity | medium 2 color | medium 2 intensity |
|---|---|---|---|---|---|---|
| Salmonella typhimurium | 10 | 24 h | gray | 1.5 | gray | 3 |
| | | 48 h | gray | 1.5 | gray | 3.5 |
| Salmonella paratyphi A | 152 | 24 h | gray | 1 | gray | 3 |
| | | 48 h | gray | 1.5 | gray | 3.5 |
| Proteus vulgaris | 15 | 24 h | — | — | — | — |
| | | 48 h | — | — | — | — |
| Serratia marcescens | 13 | 24 h | gray | 1.5 | gray | 3 |
| | | 48 h | gray | 1 | gray | 4 | intensity of coloration: arbitrary scale;
—: absence of coloration or intensity

The medium containing Tween® 20 therefore makes it possible to obtain more intense colorations for the strains of microorganisms exhibiting an esterase activity. The substrate is therefore more widely used either because it dissolves better or because it is more readily available. In view of the difference in intensity between the two media, it seems to be possible, in the presence of Tween® 20, to reduce the concentration of substrate used and hence to lower the cost incurred by the use of this type of substrate.

Example 4

Testing this Mode of Dissolution for Another Indoxyl Derivative (Chromogenic Esterase Substrate) on Gram-positive and Gram-negative Bacterial Species and Yeasts A 40 g/l stock solution of 5-bromo-4-chloro-3-indolyl octanoate (chromogenic esterase substrate) was prepared in a mixture of methanol (40%) and Tween® 20 (60%). A volume corresponding to a final concentration of 500 mg/l of substrate was then added to a supercooled gelled medium, namely a medium of the Columbia type. This medium was poured into Petri dishes.

Microorganisms originating from the Applicant's collection were inoculated from a 0.5 McFarland suspension by isolation in three quadrants. The dishes were then incubated at 37° C. for 48 hours. The colonies formed were examined visually after 24 and 48 hours of incubation. The coloration of these colonies and the intensity of this coloration were noted. The results are shown in Table 4 below.

TABLE 4

| Strain | | incubation time | medium 1 color | medium 1 intensity |
|---|---|---|---|---|
| Listeria monocytogenes | 023 | 24 h | turquoise | 2.5 |
| | | 48 h | turquoise | 2.5 |
| Listeria innocua | 029 | 24 h | — | — |
| | | 48 h | turquoise | 0.5 |
| Staphylococcus aureus | 276 | 24 h | turquoise | 2.5 |
| | | 48 h | turquoise | 3 |
| Candida albicans | 033 | 24 h | turquoise | 0.5 |
| | | 48 h | turquoise | 3 |
| Staphylococcus epidermidis | 009 | 24 h | turquoise | 2 |
| | | 48 h | turquoise | 2 |
| Salmonella spp. | | 24 h | turquoise | 2 |
| | 017 | 48 h | turquoise | 3 |
| Proteus vulgaris | 015 | 24 h | — | — |
| | | 48 h | — | — | intensity of coloration: arbitrary scale;
—: absence of coloration or intensity

In the presence of Tween 20, it is therefore possible to reveal the expression of an esterase activity in all microorganisms that exhibit it, independently of the group to which they belong. Furthermore, this mode of use is independent of the indoxyl derivative (chromogenic esterase substrate) studied.

Example 5

Replacing Methanol with Other Solvents in the Presence of Tween 20 and in the Presence of Bile Salts The methanol used in the previous Examples was replaced with two other solvents, namely dimethyl sulfoxide (DMSO) and dimethylformamide (DMF). The three solvents were tested in the presence of Tween 20 and in the presence or absence of bile salts at a final concentration of 6.5 g/l in the medium. Table 5 below shows the composition of the six media tested.

TABLE 5

| Medium | 1 | 2 | 3 | 4 | 5 | 6 |
|---|---|---|---|---|---|---|
| Solvent S of the stock solution (SS) | methanol | DMSO | DMF | methanol | DMSO | DMF |
| % of solvent S in the SS | | | | 40% | | |
| % of Tween ® 20 added to the SS of substrate | | | | 60% | | |
| Bile salt concentration of the medium | | 6.5 g/l | | | 0 g/l | |
| Final substrate concentration of the medium | | | | 500 mg/l | | |

The activity of the substrate was verified in the same way as in the previous Example, i.e. in the presence of microorganisms inoculated onto a MacConkey gelose medium containing the esterase substrate dissolved in one of the solvents mentioned above. The results are shown in Table 6 below.

TABLE 6

| Medium | | 1 | | 2 | | 3 | | 4 | | 5 | | 6 | |
|---|---|---|---|---|---|---|---|---|---|---|---|---|---|
| Strain | IT | C | I | C | I | C | I | C | I | C | I | C | I |
| Salmonella typhimurium | 24 | gray | 2 | gray | 2 | gray | 2 | gray | 2 | gray | 2 | gray | 2 |
| | 10 48 | gray | 2.5 | gray | 2.5 | gray | 2.5 | gray | 2.5 | gray | 2.5 | gray | 2.5 |
| Salmonella arizonae | 24 | gray | 2 | gray | 2.5 | gray | 2 | gray | 2 | gray | 2.5 | gray | 2 |
| | 15 48 | gray | 2.5 | gray | 3 | gray | 2.5 | gray | 2.5 | gray | 3 | gray | 2.5 |
| Pseudomonas aeruginosa | 24 | gray | 2 | gray | 2 | gray | 1 | gray | 2 | gray | 2 | gray | 1 |
| | 15 48 | gray | 2.5 | gray | 4 | gray | 3.5 | gray | 3 | gray | 4 | gray | 4 |
| Proteus vulgaris | 24 | — | — | — | — | — | — | — | — | — | — | — | — |
| | 15 48 | — | — | — | — | — | — | — | — | — | — | — | — |
| Serratia marcescens | 24 | gray | 2.5 | gray | 2 | gray | 2 | gray | 2.5 | gray | 2 | gray | 2 |
| | 38 48 | gray | 2.5 | gray | 2 | gray | 2 | gray | 2.5 | gray | 2 | gray | 2 |

I: intensity of coloration (arbitrary scale);
C: color;
IT: incubation time in hours;
—: colorless It is therefore possible to use different solvents to dissolve the esterase substrate when Tween 20 is present. Furthermore, the addition of bile salts makes no difference, whether in terms of solubility or in terms of biological results, irrespective of the solvent tested. It is concluded that the simplest mode of dissolution is to mix a solvent and Tween® 20 without the additional incorporation of bile salts.

Example 6

Testing Different Solvent S/Tween 20 Ratios

Different stock solutions of substrate are prepared in DMSO in the presence of Tween® 20. Each stock solution corresponds to a different DMSO/Tween® 20 ratio. A volume corresponding to a final concentration of 500 mg/l of substrate is then added to a supercooled gelled medium, namely MacConkey medium. Table 7 below shows the composition of the six media tested.

TABLE 7

| Medium | 1 | 2 | 3 | 4 | 5 | 6 |
|---|---|---|---|---|---|---|
| % of DMSO in the stock solution | 10% | 20% | 30% | 40% | 50% | 60% |
| % of Tween ® 20 added to the stock solution of substrate | 90% | 80% | 70% | 60% | 50% | 40% |

Microorganisms originating from the Applicant's collection were inoculated onto each of the six media described above from a 0.5 McFarland suspension by isolation in three quadrants. The dishes were incubated at 37° C. for 48 hours. The colonies formed were examined visually after 24 and 48 hours of incubation. The coloration of these colonies and the intensity of this coloration were noted. The results are shown in Table 8 below.

TABLE 8

| Medium | | 1 | | 2 | | 3 | | 4 | | 5 | | 6 | |
|---|---|---|---|---|---|---|---|---|---|---|---|---|---|
| Strain | IT | C | I | C | I | C | I | C | I | C | I | C | I |
| Salmonella |  | 24 | gray | 2.5 | gray | 2.5 | gray | 2 | gray | 3 | gray | 3 | gray | 3 |
| typhimurium | 10 | 48 | gray | 3 | gray | 3 | gray | 2.5 | gray | 3.5 | gray | 3 | gray | 3.5 |
| Salmonella |  | 24 | gray | 2.5 | gray | 2.5 | gray | 3 | gray | 3.5 | gray | 3 | gray | 3.5 |
| arizonae | 15 | 48 | gray | 2.5 | gray | 2.5 | gray | 3 | gray | 3.5 | gray | 3 | gray | 3.5 |
| Serratia |  | 24 | gray | 3 | gray | 3 | gray | 3 | gray | 4 | gray | 3.5 | gray | 3.5 |
| marcescens | 045 | 48 | gray | 4 | gray | 4 | gray | 4 | gray | 4 | gray | 4 | gray | 4 |
| Hafnia alvei |  | 24 | — | — | — | — | — | — | — | — | — | — | — | — |
|  | 025 | 48 | — | — | — | — | — | — | — | — | — | — | — | — |
| Pseudomonas |  | 24 | gray | 2 | gray | 2 | gray | 3 | gray | 3 | gray | 3 | gray | 3 |
| aeruginosa | 165 | 48 | gray | 2 | gray | 2 | gray | 2 | gray | 3 | gray | 3 | gray | 3 |
| Salmonella |  | 24 | gray | 1.5 | gray | 1.5 | gray | 2 | gray | 3 | gray | 2.5 | gray | 3 |
| paratyphi A | 006 | 48 | gray | 2 | gray | 2 | gray | 3 | gray | 3 | gray | 3 | gray | 3 |
| Salmonella |  | 24 | gray | 2 | gray | 2 | gray | 2 | gray | 3 | gray | 2 | gray | 3 |
| typhi | 118 | 48 | gray | 2 | gray | 2 | gray | 2 | gray | 3 | gray | 2 | gray | 3 |

I: intensity of coloration (arbitrary scale);
C: color;
IT: incubation time in hours;
—: colorless The six ratios tested make it possible to obtain a good substrate solubility and to reveal hydrolysis of the substrate with very acceptable intensities of coloration. Maximum intensities of coloration are obtained between the ratios 40% DMSO/60% Tween® 20 and 60% DMSO/40% Tween® 20.

Example 7

Testing the Method of Solubilization on an Esterase Substrate Having a Marker Other than an Indoxyl The substrate tested is 1,2-dihydroxyanthraquinone octanoate (2-alizarin octanoate). Different stock solutions of substrate are prepared with DMF, DMSO, methanol or methoxyethanol as solvent and in the presence of Tween® 20 in all cases. Table 9 below shows the appearance of the stock solutions according to their composition.

TABLE 9

| Solvent of the stock solution | methanol | DMSO | DMF | methoxyethanol |
|---|---|---|---|---|
| % of solvent in the stock solution |  |  | 40% |  |
| % of Tween ® 20 added to the stock solution of substrate |  |  | 60% |  |
| Appearance of the stock solution | precipitate | precipitate | total dissolution | total dissolution |

A volume corresponding to a final concentration of 100 mg/l of substrate is then added to a supercooled gelled medium, namely MacConkey medium. Iron citrate at a final concentration of 50 mg/l was also added to the medium so that the esterase activity could be revealed in the presence of an alizarin-based substrate. Only one of the stock solutions exhibiting total dissolution of the substrate was tested (stock solution in DMF). Microorganisms originating from the Applicant's collection were inoculated onto each of the two media described above from a 0.5 McFarland suspension by isolation in three quadrants. The dishes were incubated at 37° C. for 48 hours. The colonies formed were examined visually after 24 and 48 hours of incubation. The coloration of these colonies and the intensity of this coloration were noted. The results are shown in Table 10.

TABLE 10

| Strain | | incubation time | medium with DMF | |
|---|---|---|---|---|
| | | | color | intensity |
| Salmonella typhimurium |  | 24 h | mauve | 1 |
|  | 10 | 48 h | mauve | 2 |
| Salmonella enteritidis |  | 24 h | mauve | 1 |
|  | 036 | 48 h | mauve | 3 |
| Salmonella arizonae |  | 24 h | mauve | 1 |
|  | 018 | 48 h | mauve | 2 |
| Escherichia coli |  | 24 h | — | — |
|  | 002 | 48 h | — | — |

TABLE 10-continued

| Strain | | incubation time | medium with DMF | |
|---|---|---|---|---|
| | | | color | intensity |
| Serratia marcescens |  | 24 h | mauve | 3.5 |
|  | 045 | 48 h | mauve | 3.5 |
| Staphylococcus aureus |  | 24 h | mauve | 3 |
|  | 033 | 48 h | mauve | 4 |
| Pseudomonas aeruginosa |  | 24 h | mauve | 2 |

TABLE 10-continued

| Strain | incubation time | medium with DMF | |
|---|---|---|---|
| | | color | intensity |
| | 165 | 48 h | mauve | 2 |
| Salmonella gallinarum | 24 h | mauve | 0.5 |
| | 500 | 48 h | mauve | 3 | intensity of coloration: arbitrary scale;
—: absence of coloration or intensity

This mode of dissolution is therefore not specific for indoxyl esters, but can be used especially with other families of enzyme substrates.

Example 8

Testing Different FASE Derived from Tween® 20 for the Solubilization of the Esterase Substrate 5-bromo-3-indolyl Nonanoate Different stock solutions of substrate are prepared in DMSO in the presence of Tween® 20, Tween® 80 (polyethoxylated sorbitan monooleate), Tween® 60 (polyethoxylated sorbitan monostearate) or Tween® 65 (polyethoxylated sorbitan tristearate). A volume corresponding to a final concentration of 500 mg/l of substrate is then added to a supercooled gelled medium, namely MacConkey medium. Table 11 shows the composition of the media tested.

TABLE 11

| Medium | 1 | 2 | 3 | 4 |
|---|---|---|---|---|
| % of DMSO in the stock solution | 40% | 40% | 40% | 40% |
| % of Tween 20 added to the stock solution of substrate | 60% | — | — | — |
| % of Tween 60 added to the stock solution of substrate | — | 60% | — | — |
| % of Tween 65 added to the stock solution of substrate | — | — | 60% | — |
| % of Tween 80 added to the stock solution of substrate | — | — | — | 60% |

Microorganisms originating from the Applicant's collection were inoculated onto each of the six media described above from a 0.5 McFarland suspension by isolation in three quadrants. The dishes were incubated at 37° C. for 48 hours. The colonies formed were examined visually after 24 and 48 hours of incubation. The coloration of these colonies and the intensity of this coloration were noted. The results are shown in Table 12.

TABLE 12

| Medium | | 1 | | 2 | | 3 | | 4 | |
|---|---|---|---|---|---|---|---|---|---|
| Strain | IT | C | I | C | I | C | I | C | I |
| Salmonella | | 24 h | gray | 2.5 | gray | 2 | — | — | gray | 2 |
| typhimurium | 10 | 48 h | gray | 3 | gray | 2 | — | — | gray | 2 |
| Salmonella | | 24 h | gray | 2.5 | gray | 1 | — | — | gray | 1 |
| arizonae | 15 | 48 h | gray | 3 | gray | 2 | — | — | gray | 3 |
| Salmonella | | 24 h | gray | 1.5 | gray | 1 | — | — | gray | 1 |
| paratyphi A | 006 | 48 h | gray | 3.5 | gray | 2 | — | — | gray | 3 |
| Salmonella | | 24 h | gray | 2 | gray | 1 | — | — | gray | 1 |
| typhi | 118 | 48 h | gray | 2.5 | gray | 2 | — | — | gray | 2 |
| Pseudomonas | | 24 h | gray | 3 | gray | 0.5 | — | — | gray | 4 |
| aeruginosa | 165 | 48 h | gray | 3 | gray | 2 | — | — | gray | 4 |
| Hafnia alvei | | 24 h | — | — | — | — | — | — | — | — |
| | 025 | 48 h | — | — | — | — | — | — | — | — |

I: intensity of coloration (arbitrary scale);
C: color;
IT: incubation time;
—: colorless Note: Different Tween®/solvent ratios were prepared for each Tween® tested. However, only one ratio is listed in this Example because the results were very similar, irrespective of the ratio studied.

Tween® 20, Tween® 80 and Tween® 60 make it possible to obtain a good substrate solubility and to reveal hydrolysis of the substrate with very acceptable intensities of coloration.

Example 9

Comparative Stability of Gelled Media Containing the Esterase Substrate 5-bromo-3-indolyl Nonanoate Solubilized or Not Solubilized in the Presence of Tween® 20

Two stock solutions of substrate were prepared, one having a concentration of 40 g/l in methanol in the presence of 6.5 g/l of no. 3 bile salts, and the other having a concentration of 40 g/l in a mixture of DMSO (40%) and Tween® 20 (60%). A volume corresponding to a final concentration of 500 mg/l of substrate was then added to a supercooled gelled medium, namely MacConkey medium. These two media were poured into Petri dishes of diameter 90 mm and stored at +4° C. for 8 weeks. After one week, two weeks, four weeks and eight weeks, two media like those described above were prepared for immediate use.

Microorganisms originating from the Applicant's collection were inoculated from a 0.5 McFarland suspension, by isolation in three quadrants, onto the two media prepared for immediate use and the two media stored at +4° C. The dishes were incubated at 37° C. for 48 hours. The colonies formed were examined visually after 24 and 48 hours of incubation. The coloration of these colonies and the intensity of this coloration were noted. The results are shown in the Tables below.

TABLE 13

| Medium Strain | IT | fresh methanol bile salts C | fresh methanol bile salts I | stored for 1 week methanol bile salts C | stored for 1 week methanol bile salts I | fresh DMSO Tween 20 C | fresh DMSO Tween 20 I | stored for 1 week DMSO Tween 20 C | stored for 1 week DMSO Tween 20 I |
|---|---|---|---|---|---|---|---|---|---|
| Salmonella typhimurium | 24 h | gray | 0.5 | gray | 0.5 | gray | 3 | gray | 3 |
| 10 | 48 h | gray | 1.5 | gray | 1.5 | gray | 4 | gray | 4 |
| Salmonella arizonae | 24 h | gray | 1 | gray | 1 | gray | 3 | gray | 3 |
| 15 | 48 h | gray | 1.5 | gray | 1.5 | gray | 4 | gray | 4 |
| Salmonella paratyphi A | 24 h | — | — | — | — | gray | 2 | gray | 2 |
| 006 | 48 h | gray | 0.5 | gray | 0.5 | gray | 4 | gray | 4 |
| Salmonella typhi | 24 h | gray | 0.5 | gray | 0.5 | gray | 3 | gray | 3 |
| 118 | 48 h | gray | 1.5 | gray | 1.5 | gray | 4 | gray | 4 |
| Pseudomonas aeruginosa | 24 h | gray | 1 | gray | 1 | gray | 2 | gray | 2 |
| 165 | 48 h | gray | 1 | gray | 1 | gray | 3 | gray | 3 |
| Hafnia alvei | 24 h | — | — | — | — | — | — | — | — |
| 025 | 48 h | — | — | — | — | — | — | — | — |

TABLE 14

| Medium Strain | IT | fresh methanol bile salts C | fresh methanol bile salts I | stored for 2 weeks methanol bile salts C | stored for 2 weeks methanol bile salts I | fresh DMSO Tween 20 C | fresh DMSO Tween 20 I | stored for 2 weeks DMSO Tween 20 C | stored for 2 weeks DMSO Tween 20 I |
|---|---|---|---|---|---|---|---|---|---|
| Salmonella typhimurium 10 | 24 h | gray | 0.5 | gray | 0.5 | gray | 3 | gray | 3 |
| | 48 h | gray | 1.5 | gray | 1.5 | gray | 4 | gray | 4 |
| Salmonella arizonae 15 | 24 h | gray | 1 | gray | 0.1 | gray | 3 | gray | 3 |
| | 48 h | gray | 1.5 | gray | 0.5 | gray | 4 | gray | 4 |
| Salmonella paratyphi A 006 | 24 h | — | — | — | — | gray | 2 | gray | 2 |
| | 48 h | gray | 0.5 | gray | 0.1 | gray | 4 | gray | 4 |
| Salmonella typhi 118 | 24 h | gray | 0.5 | — | — | gray | 3 | gray | 3 |
| | 48 h | gray | 1.5 | gray | 0.5 | gray | 4 | gray | 4 |
| Pseudomonas aeruginosa 165 | 24 h | gray | 1 | gray | 1 | gray | 2 | gray | 2 |
| | 48 h | gray | 1 | gray | 1 | gray | 3 | gray | 3 |
| Hafnia alvei 025 | 24 h | — | — | — | — | — | — | — | — |
| | 48 h | — | — | — | — | — | — | — | — |

TABLE 15

| Medium Strain | IT | fresh methanol bile salts C | fresh methanol bile salts I | stored for 4 weeks methanol bile salts C | stored for 4 weeks methanol bile salts I | fresh DMSO Tween 20 C | fresh DMSO Tween 20 I | stored for 4 weeks DMSO Tween 20 C | stored for 4 weeks DMSO Tween 20 I |
|---|---|---|---|---|---|---|---|---|---|
| Salmonella typhimurium 10 | 24 h | gray | 0.5 | — | — | gray | 3 | gray | 3 |
| | 48 h | gray | 1.5 | gray | 0.5 | gray | 4 | gray | 4 |
| Salmonella arizonae 15 | 24 h | gray | 1 | gray | 0.1 | gray | 3 | gray | 3 |
| | 48 h | gray | 1.5 | gray | 0.5 | gray | 4 | gray | 4 |
| Salmonella paratyphi A 006 | 24 h | — | — | — | — | gray | 2 | gray | 2 |
| | 48 h | gray | 0.5 | gray | 0.1 | gray | 4 | gray | 4 |
| Salmonella typhi 118 | 24 h | gray | 0.5 | — | — | gray | 3 | gray | 3 |
| | 48 h | gray | 1.5 | gray | 0.5 | gray | 4 | gray | 4 |
| Pseudomonas aeruginosa 165 | 24 h | gray | 1 | gray | 0.5 | gray | 2 | gray | 2 |
| | 48 h | gray | 1 | gray | 1 | gray | 3 | gray | 3 |
| Hafnia alvei 025 | 24 h | — | — | — | — | — | — | — | — |
| | 48 h | — | — | — | — | — | — | — | — |

TABLE 16

| Medium | | fresh methanol bile salts | | stored for 8 weeks methanol bile salts | | fresh DMSO Tween 20 | | stored for 8 weeks DMSO Tween 20 | |
|---|---|---|---|---|---|---|---|---|---|
| Strain | IT | C | I | C | I | C | I | C | I |
| Salmonella typhimurium | 24 h | gray | 0.5 | — | — | gray | 3 | gray | 2.5 |
| | 10 48 h | gray | 1.5 | gray | 0.5 | gray | 4 | gray | 3.5 |
| Salmonella arizonae | 24 h | gray | 1 | — | — | gray | 3 | gray | 3 |
| | 15 48 h | gray | 1.5 | gray | 0.5 | gray | 4 | gray | 3 |
| Salmonella paratyphi A | 24 h | — | — | — | — | gray | 2 | gray | 1.5 |
| | 006 48 h | gray | 0.5 | — | — | gray | 4 | gray | 3 |
| Salmonella typhi | 24 h | gray | 0.5 | — | — | gray | 3 | gray | 2 |
| | 118 48 h | gray | 1.5 | gray | 0.5 | gray | 4 | gray | 3 |
| Pseudomonas aeruginosa | 24 h | gray | 1 | gray | 0.5 | gray | 2 | gray | 2 |
| | 165 48 h | gray | 1 | gray | 1 | gray | 3 | gray | 3 |
| Hafnia alvei | 24 h | — | — | — | — | — | — | — | — |
| | 025 48 h | — | — | — | — | — | — | — | — |

I: intensity of coloration (arbitrary scale);
C: color;
IT: incubation time;
—: colorless The medium containing the substrate dissolved in a mixture of methanol and bile salts exhibits a very substantial drop in the expression of esterase activity after storage for 2 weeks. This drop is amplified over time. The medium containing the substrate dissolved in a mixture of DMSO and Tween 20 exhibits a constant expression of esterase activity over time for up to at least six weeks. After eight weeks there is a slight but not prohibitive drop in the expression of esterase activity. Tween 20 therefore makes it possible to stabilize the esterase substrate and makes it easier to store and use culture media containing this type of substrate.

Note: In the above Examples, the numbers following the strains correspond to the number of each strain referenced in the Applicant's collection. The intensity of coloration corresponds to an arbitrary scale defined as follows:

| | |
|---|---|
| 0 | no activity |
| 0.1 | trace of coloration |
| 0.5 | very pale coloration |
| 1 | distinct coloration of low intensity |
| 2 | clear coloration of medium intensity |
| 3 | intense coloration |
| 4 | very intense coloration |

Example 10

Comparative Stability of Gelled Media Containing the Osidase Substrate 6-chloro-3-indolyl-β-N-acetylglucosaminide Solubilized or Not Solubilized in the Presence of Tween® 20

Two stock solutions of substrate were prepared, one having a concentration of 50 g/l in DMF and the other having a concentration of 50 g/l in a mixture of DMF (40%) and Tween® 20 (60%). A volume corresponding to a final concentration of 175 mg/l of substrate was then added to a supercooled gelled medium, namely Columbia medium not supplemented with blood. These two media were poured into Petri dishes of diameter 90 mm and stored at +4° C. for 8 weeks. After three weeks, six weeks, nine weeks and twelve weeks, two media like those described above were prepared for immediate use.

Microorganisms originating from the Applicant's collection were inoculated from a 0.5 McFarland suspension, by isolation in three quadrants, onto the two media prepared for immediate use and the two media stored at +4° C. The dishes were incubated at 37° C. for 48 hours. The colonies formed were examined visually after 24 and 48 hours of incubation. The coloration of these colonies and the intensity of this coloration were noted. The results are shown in the Tables below.

TABLE 17

| Medium | | fresh DMF | | stored for 3 weeks DMF | | fresh DMF Tween 20 | | stored for 3 weeks DMF Tween 20 | |
|---|---|---|---|---|---|---|---|---|---|
| Strain | IT | C | I | C | I | C | I | C | I |
| Listeria innocua | 24 h | M | 2 | M | 1.5 | M | 2 | M | 2 |
| | 36 48 h | M | 3 | M | 3 | M | 3 | M | 3 |
| Listeria ivanovii | 24 h | M | 1.5 | M | 1 | M | 1.5 | M | 1.5 |
| | 18 48 h | M | 2.5 | M | 2.5 | M | 2.5 | M | 2.5 |
| Listeria monocytogenes | 24 h | M | 2 | M | 1.5 | M | 2 | M | 2 |
| | 23 48 h | M | 3 | M | 3 | M | 3 | M | 3 |

TABLE 17-continued

| Medium Strain | IT | fresh DMF C | fresh DMF I | stored for 3 weeks DMF C | stored for 3 weeks DMF I | fresh DMF Tween 20 C | fresh DMF Tween 20 I | stored for 3 weeks DMF Tween 20 C | stored for 3 weeks DMF Tween 20 I |
|---|---|---|---|---|---|---|---|---|---|
| Staphylococcus aureus | 20 | 24 h 48 h | — — | — — | — — | — — | — — | — — | — — |
| Pseudomonas aeruginosa | 165 | 24 h 48 h | — — | — — | — — | — — | — — | — — | — — |

TABLE 18

| Medium Strain | IT | fresh DMF C | fresh DMF I | stored for 6 weeks DMF C | stored for 6 weeks DMF I | fresh DMF Tween 20 C | fresh DMF Tween 20 I | stored for 6 weeks DMF Tween 20 C | stored for 6 weeks DMF Tween 20 I |
|---|---|---|---|---|---|---|---|---|---|
| Listeria innocua | 36 | 24 h 48 h | M M | 2 3 | M M | 1 2 | M M | 2 3 | M M | 2 3 |
| Listeria ivanovii | 18 | 24 h 48 h | M M | 1.5 2.5 | M M | 0.5 2 | M M | 1.5 2.5 | M M | 1.5 2.5 |
| Listeria monocytogenes | 23 | 24 h 48 h | M M | 2 3 | M M | 1 2 | M M | 2 3 | M M | 2 3 |
| Staphylococcus aureus | 20 | 24 h 48 h | — — | — — | — — | — — | — — | — — | — — |
| Pseudomonas aeruginosa | 165 | 24 h 48 h | — — | — — | — — | — — | — — | — — | — — |

TABLE 19

| Medium Strain | IT | fresh DMF C | fresh DMF I | stored for 9 weeks DMF C | stored for 9 weeks DMF I | fresh DMF Tween 20 C | fresh DMF Tween 20 I | stored for 9 weeks DMF Tween 20 C | stored for 9 weeks DMF Tween 20 I |
|---|---|---|---|---|---|---|---|---|---|
| Listeria innocua | 36 | 24 h 48 h | M M | 2 3 | M M | 0.5 1 | M M | 2 3 | M M | 1.5 2.5 |
| Listeria ivanovii | 18 | 24 h 48 h | M M | 1.5 2.5 | M M | — 0.5 | M M | 1.5 2.5 | M M | 1 2.5 |
| Listeria monocytogenes | 23 | 24 h 48 h | M M | 2 3 | M M | 0.5 0.5 | M M | 2 3 | M M | 1 2 |
| Staphylococcus aureus | 20 | 24 h 48 h | — — | — — | — — | — — | — — | — — | — — |
| Pseudomonas aeruginosa | 165 | 24 h 48 h | — — | — — | — — | — — | — — | — — | — — |

TABLE 20

| Medium Strain | IT | fresh DMF C | fresh DMF I | stored for 12 weeks DMF C | stored for 12 weeks DMF I | fresh DMF Tween 20 C | fresh DMF Tween 20 I | stored for 12 weeks DMF Tween 20 C | stored for 12 weeks DMF Tween 20 I |
|---|---|---|---|---|---|---|---|---|---|
| Listeria innocua | 36 | 24 h 48 h | M M | 2 3 | M M | — 0.5 | M M | 2 3 | M M | 1 2.5 |
| Listeria ivanovii | 18 | 24 h 48 h | M M | 1.5 2.5 | M M | — — | M M | 1.5 2.5 | M M | 1 2 |
| Listeria monocytogenes | 23 | 24 h 48 h | M M | 2 3 | M M | — — | M M | 2 3 | M M | 1 2 |
| Staphylococcus aureus | 20 | 24 h 48 h | — — | — — | — — | — — | — — | — — | — — |

TABLE 20-continued

| Medium | | fresh DMF | | stored for 12 weeks DMF | | fresh DMF Tween 20 | | stored for 12 weeks DMF Tween 20 | |
|---|---|---|---|---|---|---|---|---|---|
| Strain | IT | C | I | C | I | C | I | C | I |
| *Pseudomonas aeruginosa* 165 | 24 h | — | — | — | — | — | — | — | — |
|  | 48 h | — | — | — | — | — | — | — | — |

I: intensity of coloration (arbitrary scale);
C: color;
IT: incubation time;
M: magenta;
—: colorless The medium containing the substrate dissolved in DMF alone exhibits a very substantial drop in the expression of β-N-acetylglucosaminidase activity after storage for three weeks. This drop is amplified over time. Activity can no longer be detected after twelve weeks. The medium containing the substrate dissolved in a mixture of DMF and Tween 20 exhibits a constant expression of β-N-acetylglucosaminidase activity over time up to at least six weeks. After nine and twelve weeks, there is a slight but not prohibitive drop in the expression of β-N-acetylglucosaminidase activity. Tween 20 therefore makes it possible to stabilize the β-N-acetylglucosaminidase substrate and makes it easier to store and use culture media containing this type of substrate.

In the above Examples, the numbers following the strains correspond to the number of each strain referenced in the Applicant's collection. The intensity of coloration corresponds to an arbitrary scale defined as follows:

| 0 | no activity |
|---|---|
| 0.1 | trace of coloration |
| 0.5 | very pale coloration |
| 1 | distinct coloration of low intensity |
| 2 | clear coloration of medium intensity |
| 3 | intense coloration |
| 4 | very intense coloration |

The invention claimed is:

1. A medium for detecting and/or identifying microorganisms with an enzymatic activity selected from the group consisting of esterase activity, osidase activity, peptidase activity, sulfatase activity, phosphatase activity, and mixtures thereof, said medium comprising a culture medium and at least one chromogenic or fluorogenic substrate selected from the group consisting of esterase substrate, osidase substrate, peptidase substrate, sulfatase substrate, phosphatase substrate, and mixtures thereof with the exclusion of substrates comprising a 4-[2-(4-octanoyloxy-3,5-dimethoxyphenyl)vinyl]quinolinium-1-(propan-3-ylcarboxylic acid) cation and an anion, the detecting and/or identifying being based on revealing the presence of the enzymatic activity, wherein said medium:
is in a stable, ready-to-use liquid or gel form; and contains:
at least one fatty acid sorbitan ester (FASE) or at least one fatty acid (FA) or an FASE/FA mixture as an emulsifying stabilizer, the concentration of (FASE) in the medium in % by weight is greater than or equal to 0.5% and less than or equal to 5%, and
at least one solvent (S).

2. The medium according to claim 1, obtained by mixing at least one stock solution of substrate in the solvent S, with FASE, FA or an FASE/FA mixture, and with at least one component of the culture medium.

3. The medium according to claim 1, wherein the FASE is selected from the group consisting of:
polyethoxylated sorbitan monolaurate containing 20 units of ethylene oxide (EO); polyethoxylated sorbitan monopalmitate (20 EO);
polyethoxylated sorbitan monostearate (20 EO);
polyethoxylated sorbitan tristearate (20 EO);
polyethoxylated sorbitan monooleate (20 EO);
polyethoxylated sorbitan sesquioleate (20 EO);
polyethoxylated sorbitan trioleate (20 EO); and mixtures thereof.

4. The medium according to claim 1, wherein the FA is selected from the group consisting of C4–C20 saturated or unsaturated fatty acids, and mixtures thereof.

5. The medium according to claim 1, also comprising at least one anionic surfactant.

6. The medium according to claim 1, wherein the chromogenic or fluorogenic substrate consists of a target part for the enzyme and a chromophoric or fluorophoric part, the target part being selected from the group consisting of:
glycosides consisting of mono-, di- and/or polysaccharide units linked in a α- or β-position to a hydroxyl group of the fluorophoric or chromophoric part;
α-amino acids or peptides;
organic acids such as —O—CO(CH$_2$)$_n$—CH$_3$, where n is between 0 and 20; and
a sulfate, a phosphate, a pyrosulfate, a pyrophosphate and a phosphor-diester, and the chromophoric or fluorophoric part being selected from the group consisting of:
quinones/anthraquinones and derivatives;
amino- and hydroxycoumarins and derivatives;
fluoresceins and derivatives; and
indoxyls and derivatives.

7. The medium according to claim 1, wherein the solvent S is selected from the group consisting of:
alcohols;
amides;
sulfur-containing solvents;
aqueous solvents; and
mixtures thereof.

8. The medium according to claim 1, wherein the proportion by weight of fatty acid sorbitan ester(s) (FASE) to solvent (S) is between 20:80 and 80:20.

9. The medium according to claim 1, wherein the concentration of substrate in the medium is defined as follows in mg/l:

1 ≦ substrate ≦ 2000.

10. The medium according to claim 1, wherein the culture medium is selected from the group consisting of
    selective media of the type consisting of MacConkey, Columbia ANC, PALCAM and Sabouraud gentamycin-chloramphenicol media; and
    non-selective media of the type consisting of Columbia ± blood, trypcase soya, nutrient gelose and Sabouraud media.

11. The medium according to claim 1, wherein the microorganisms are of the genus *Salmonella, Pseudomonas, Listeria, Staphylococcus, Enterococcus* or *Candida*.

12. The medium according to claim 1, wherein the concentration of (FASE) in the medium in % by weight is greater than or equal to 1.5% and less than or equal to 3.5%.

13. A method of obtaining a medium for detecting/identifying micro-organisms with an enzymatic activity selected from the group consisting of esterase activity, osidase activity, peptidase activity, sulfatase activity, phosphatase activity, and mixtures thereof, said medium comprising a culture medium and at least one chromogenic or fluorogenic substrate selected from the group consisting of esterase substrate, osidase substrate, peptidase substrate, sulfatase substrate, phosphatase substrate, or mixtures thereof, with the exclusion of substrates comprising a 4-[2-(4-octanoyloxy-3,5-dimethoxyphenyl)vinyl]quinolinium-1-(propan-3-ylcarboxylic acid) cation and an anion, the detecting and/or identifying being based on revealing the presence of the enzymatic activity,
    wherein said medium:
        is in a stable, ready-to-use liquid or gel form; and contains:
            at least one fatty acid sorbitan ester (FASE) or at least one fatty acid (FA) or an FASE/FA mixture as an emulsifying stabilizer, the concentration of (FASE) in the medium in % by weight is greater than or equal to 0.5% and less than or equal to 5%, and
            at least one solvent (S)
    said method comprising the steps of:
        preparing at least one stock solution of the chromogenic or fluorogenic substrate in the solvent S and of at least one FASE, FA or FASE/FA mixture,
        adding the stock solution to the culture medium, and
        homogenizing the stock solution and the culture medium.

14. The method according to claim 13, wherein the concentration of (FASE) in the medium in % by weight is greater than or equal to 1.5% and less than or equal to 3.5%.

15. A method for detection/identification of microorganisms with an enzymatic activity selected from the group consisting of esterase activity, osidase activity, peptidase activity, sulfatase activity, phosphatase activity, or mixtures thereof the method comprising stabilizing a medium (liquid or gel) with a fatty acid sorbitan ester (FASE), fatty acid (FA) or FASE/FA as an emulsifying stabilizer, the FASE having a concentration in the medium in % by weight of greater than or equal to 0.5% and less than or equal to 5%, the medium comprising a culture medium and at least one chromogenic or fluorogenic substrate selected from the group consisting of esterase substrate, osidase substrate, peptidase substrate, sulfatase substrate, phosphatase substrate, and mixtures thereof with the exclusion of substrates comprising a 4-[2-(4-octanoyloxy-3,5-dimethoxyphenyl)vinyl]quinolinium-1-(propan-3-ylcarboxylic acid) cation and an anion, in association with at least one solvent S for the chromogenic or fluorogenic substrate present in the medium;
    inoculating the culture medium with microorganisms to be detected/identified;
    incubating the inoculated medium under appropriate conditions;
    determining colorations around colonies in the medium; and
    correlating the colorations around the colonies to reveal hydrolysis of the chromogenic or fluorogenic substrate by the microorganisms and detect/identify the microorganisms.

16. The method according to claim 15, wherein the concentration of (FASE) in the medium in % by weight is greater than or equal to 1.5% and less than or equal to 3.5%.

* * * * *